United States Patent [19]

Töpfl

[11] Patent Number: 4,992,549

[45] Date of Patent: Feb. 12, 1991

[54] HERBICIDAL COMPOSITIONS

[75] Inventor: Werner Töpfl, Dornach, Switzerland

[73] Assignee: Ciba-Geigy Corporation, Ardsley, N.Y.

[21] Appl. No.: 451,482

[22] Filed: Dec. 15, 1989

Related U.S. Application Data

[62] Division of Ser. No. 245,602, Sep. 19, 1988, Pat. No. 4,904,783, which is a division of Ser. No. 919,514, Nov. 24, 1986, Pat. No. 4,786,315, which is a division of Ser. No. 641,091, Aug. 15, 1984, Pat. No. 4,639,264.

[30] Foreign Application Priority Data

Aug. 26, 1983 [CH] Switzerland .................. 4669/83

[51] Int. Cl.$^5$ .................. C07D 251/16; C07D 251/18; C07D 401/02; C07D 403/02
[52] U.S. Cl. ..................... 544/213; 540/598; 540/542; 544/195; 544/113; 544/205; 544/206; 544/207; 544/211; 544/212; 544/204; 544/58.5; 544/60; 544/83; 544/57; 544/157; 544/58.4
[58] Field of Search ............... 540/598, 542; 544/195, 544/113, 205, 206, 207, 211, 212, 204, 58.5, 60, 83, 57, 157, 213, 58.4

[56] References Cited

U.S. PATENT DOCUMENTS 4,629,494  12/1986  Shapiro ................................ 71/92

FOREIGN PATENT DOCUMENTS 0084224  12/1982  European Pat. Off. .

Primary Examiner—John M. Ford
Attorney, Agent, or Firm—Kevin T. Mansfield; Edward McC. Roberts

[57] ABSTRACT

Aminotriazines of the formula

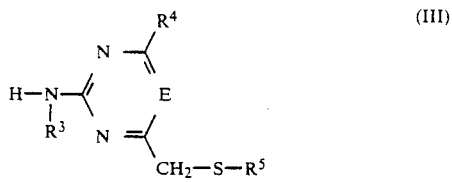

wherein

E is nitrogen,

Z is oxygen or sulfur, $R^3$ is hydrogen, $C_1$-$C_4$-alkyl, $C_3$-$C_4$-alkenyl or $C_1$-$C_4$-alkoxy, $R^4$ is hydrogen, halogen, $C_1$-$C_4$-alkyl, $C_1$-$C_4$haloalkyl, $C_1$-$C_4$-haloalkoxy, $C_1$-$C_4$-alkylthio, $C_2$-$C_4$alkoxyalkyl, $C_2$-$C_4$-alkoxyalkoxy, cyclopropyl, -$NH_2$, $C_1$-$C_4$-alkylamino, di-$C_1$-$C_4$-alkylamino, or a saturated 5- to 7-membered nitrogen heterocycle bound by way of the nitrogen atom and selected from pyrrolidine, piperidine, morpholine, thiomorpholine, piperazine and hexamethyleneimine, $R^5$ is cyano, —CZ—$R^{13}$,

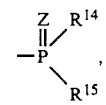

or an unsaturated hyeterocycle selected from imidazole, triazole, pyridine, pyrimidine, thiazole, oxazole, thiadiazole, oxadiazole, pyridazine, thiophene or furan, as well as partially unaturated derivatives thereof which are unsubstituted or substituted by a radical selected from the group consisting of halogen, $C_1$-$C_4$-alkyl, $C_1$-$C_4$-alkoxy and $C_1$-$C_4$-haloalkyl, $R^{13}$ is $C_1$-$C_4$-alkyl, $C_1$-$C_4$-alkoxy, $C_1$-$C_4$-alkylthio, phenyl, di-$C_1$-$C_4$-alkylamino, or a saturated 5- to 7-membered nitrogen heterocycle bound by way of the nitrogen atom and selected from pyrrolidine, piperidine, morpholine, thiomorpholine, piperazine and hexamethyleneimine and $R^{14}$ and $R^{15}$ independently of one another are $C_1$-$C_4$-alkyl, $C_1$-$C_4$-alkoxy, $C_3$-$C_4$-alkoxyalkoxy, $C_3$-$C_4$-alkenyloxy, $C_1$-$C_6$-alkylamino or di-$C_1$-$C_4$-alkylamino which are useful in preparing herbicidal sulfonylureas.

3 Claims, No Drawings

HERBICIDAL COMPOSITIONS

This is a division of application Ser. No. 245,602, now U.S. Pat. No. 4,904,783, filed on Sept. 19, 1988, which is a division of application Ser. No. 919,514, filed Nov. 24, 1986, now U.S. Pat. No. 4,786,315, which is a division of Ser. No. 641,091, filed Aug. 15, 1984, now U.S. Pat. No. 4,639,264.

The present invention relates to novel, herbicidally effective and plant-growth-regulating N-arylsulfonyl-N'(4-mercaptomethyl-pyrimidinyl- and triazinyl)-urea derivatives, to processes for producing them, to compositions containing them as active ingredients, and to the use thereof for controlling weeds, in particular selectively, in crops of cultivated plants, or for regulating and inhibiting plant growth. Furthermore, the invention relates also to novel 2-amino-4-mercaptomethyl-pyrimidine and -triazine derivatives produced as intermediates. The N-arylsulfonyl-N'-(4-mercaptomethyl-pyrimidinyl-and-triazinyl)-ureas according to the invention correspond to the formula I

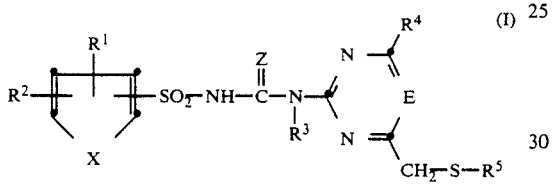

wherein

E is nitrogen or —CH=,

X is oxygen, sulfur, —NR$^3$—, —N=CR$^3$—, —CH=CH— or

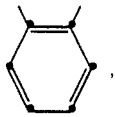

Z is oxygen or sulfur, is hydrogen, halogen, nitro, ethinyl, —NR$^{16}$R$^{17}$, —CR$^6$—di—C$_4$—alkoxy,

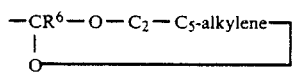

—CW—R$^6$, —SO$_2$—NR$^7$R$^8$, —CO—R$^9$, —Y$_m$—R$^{10}$, —SO$_2$—R$^{11}$ or O-SO$_2$R$^{12}$, in which m is zero or 1, R$^2$ is hydrogen, halogen, C$_1$-C$_4$-alkyl, C$_1$-C$_4$-alkoxy, C$_1$-C$_4$-haloalkyl or nitro, R$^3$ is hydrogen, C$_1$-C$_4$-alkyl, C$_3$-C$_4$-alkenyl or C$_1$-C$_4$-alkoxy, R$^4$ is hydrogen, halogen, C$_1$-C$_4$-alkyl, C$_1$-C$_4$-alkoxy, C$_1$-C$_4$haloalkyl, C$_1$-C$_4$-haloalkoxy, C$_1$-C$_4$-alkylthio, C$_2$-C$_4$-alkoxyalkyl, C$_2$-C$_4$-alkoxyalkoxy, cyclopropyl, NH$_2$, C$_1$-C$_4$-alkylamino, di-C$_1$-C$_4$-alkylamino, or a saturated 5- to 7-membered nitrogen heterocycle which is bound by way of the nitrogen atom and which can contain a further hetero atom, R$^5$ is cyano, —CZ—R$^{13}$,

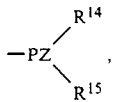

or an unsaturated heterocycle unsubstituted or substituted by a radical selected from the group comprising: halogen, C$_1$-C$_4$-alkyl, C$_1$-C$_4$-alkoxy or C$_1$-C$_4$-haloalkyl, R$^6$ is hydrogen, C$_1$-C$_4$-alkyl, C$_1$-C$_4$-haloalkyl, C$_3$-C$_6$-cycloalkyl, C$_4$-C$_7$-cycloalkylalkyl or C$_2$-C$_4$-alkoxyalkyl, R$^7$ and R$^{16}$ independently of one another are hydrogen, C$_1$-C$_4$-alkyl, C$_1$-C$_1$-cyanoalkyl or C$_1$-C$_4$-alkoxy, R$^8$ and R$^{17}$ independently of one another are hydrogen, C$_1$-C$_4$-alkyl, C$_3$-C$_4$-alkenyl or C$_1$-C$_4$-alkoxy, or R$^7$ and R$^8$ as well as R$^{16}$ and R$^{17}$ independently of one another form, together with the nitrogen atom binding them, a 5- to 7-membered saturated nitrogen heterocycle, which can contain a further hetero atom, R$^9$ is C$_1$-C$_4$-alkoxy, C$_3$-C$_6$-C$_3$-C$_6$-alkinyloxy, C$_2$-C$_6$-haloalkoxy, C$_1$-C$_4$-cyanoalkoxy, C$_1$-C$_4$-alkylthio, C$_3$-C$_4$-alkenylthio, C$_3$-C$_4$-alkinylthio, C$_5$-C$_6$-cyclo-alkoxy, C$_4$-C$_7$-cycloalkylalkoxy, —NR$^7$R$^8$ or C$_2$-C$_6$-alkoxyalkoxy, R$^{10}$ is C$_3$-C$_4$-alkenyl, C$_2$-C$_4$-alkyl, C$_2$-C$_4$-alkenyl mono- or polysubstituted by halogen, cyano, C$_1$-C$_4$-alkoxy or -SO -alkyl, or is C$_1$-C$_4$-alkyl mono- or polysubstituted by halogen, cyano, nitro, C$_1$-C$_4$-alkoxy, C$_1$-C$_4$-haloalkoxy, C$_1$-C$_4$-haloalkylthio, —SO$_n$—C$_1$-C$_4$-alkyl, —T—CX—R$^{18}$,

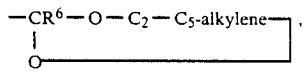

—CO—R$^6$, —CO—R$^9$ or —SO$_2$—NR$^7$R$^8$, in which n is zero, 1 or 2,

R$^{11}$ is C$_2$-C$_4$-haloalkoxy,

R$^{12}$ is C$_1$-C$_4$-alkyl, C$_1$-C$_4$-haloalkyl or —NR$^{16}$R$^{17}$,

R$^{13}$ is C$_1$-C$_1$-C$_4$-alkoxy, C$_1$-C$_4$-alkylthio, phenyl, di-C$_1$-C$_4$-alkylamino, or a saturated, 5- to 7-membered nitrogen heterocycle which is bound by way of the nitrogen atom and which can contain a further hetero atom, R$^{14}$ and R$^{15}$ independently of one another are C$_1$-C$_4$-alkyl, C$_1$-C$_4$-alkoxy, C$_3$-C$_4$-alkoxyalkoxy, C$_3$-C$_4$-alkenyloxy, C$_1$-C$_6$-alkylthio, C$_1$-C$_4$-alkylamino or di-C$_1$-C$_4$-alkylamino, R$^{18}$ is C$_1$-C$_4$-alkyl, C$_1$-C$_4$-haloalkyl, C$_1$-C$_4$-alkoxy, C$_1$-C$_4$-alkylthio or —NR$^{16}$R$^{17}$, T is oxygen or sulfur, W is oxygen or =N—O—R$^3$, and Y is oxygen, sulfur, —SO— or —SO$_2$—;

and the invention relates also to the salts of these compounds.

Urea compounds, triazine compounds and pyrimidine compounds having herbicidal activity are in general known. Sulfonylurea compounds having a herbicidal and plant-growth-regulating action have been recently described for example in the European Patent Application Nos. 44807 and 44808.

By alkyl in the definitions is meant straight-chain or branched-chain alkyl, for example: methyl, ethyl, n-propyl, i-propyl or the four isomeric butyl groups.

And by alkoxy is meant: methoxy, ethoxy, n-propyloxy, i-propyloxy, the four isomeric butyloxy groups, n-amyloxy, i-amyloxy, 2-amyloxy or 3-amyloxy, especially however methoxy, ethoxy or i-propyloxy.

Examples of alkylthio are: methylthio, ethylthio, n-propylthio, i-propylthio, n-butylthio or n-pentylthio, particularly methylthio or ethylthio.

Examples of alkylsulfinyl are: methylsulfinyl, ethylsulfinyl, n-propylsulfinyl and n-butylsulfinyl, in particular methylsulfinyl and ethylsulfinyl.

Examples of alkylsulfonyl are: methylsulfonyl, ethylsulfonyl or n-propylsulfonyl, especially methylsulfonyl and ethylsulfonyl.

Halogen in the definitions themselves, as well as halogen as a moiety in haloalkoxy, haloalkyl or haloalkylthio, is fluorine, chlorine and bromine, preferably however fluorine or chlorine.

The aryl moieties of the active substances of the formula I, which are bound to the sulfonyl bridge, are characterised by the following basic aromatic ring systems: thiophene, furan, pyridine, pyrrole, phenyl or naphthalene. The phenyl ring is preferred.

Examples of the nitrogen heterocycles defined under $R^4$ and $R^{13}$ are rings bound by way of the nitrogen atom of the following fundamental types: pyrrolidine, piperidine, morpholine, thiomorpholine or piperazine or hexamethyleneimine.

The unsaturated heterocycles defined under $R^5$ embrace, within the scope of the present invention, for example the following basic ring systems: imidazole, triazole, pyridine, pyrimidine, thiazole, oxazole, thiadiazole, oxadiazole, pyridazine, thiophene or furan, as well as partially hydrogenated derivatives thereof. Preferred unsaturated heterocyclic substituents within the definition of $R^5$ are 4,5-dihydrothiazol-2-yl, 2H-1,2,4-triazol-3-yl, 1-methyl-imidazol-2-yl, 2-pyridinyl and 2-pyrimidinyl.

Examples of cycloalkyl are: cyclopropyl, cyclobutyl, cyclopentyl and cyclohexyl, preferably however cyclopentyl and cyclohexyl. Preferred cycloalkylalkyl radicals are cyclopropylmethyl, cyclopentylmethyl and cyclohexylmethyl. Alkoxyalkyl groups are represented by: methoxymethyl, ethoxymethyl, methoxyethyl and ethoxyethyl, especially methoxyethyl. Alkoxyalkoxy groups within the scope of the present invention are: methoxymethoxy, ethoxymethoxy, methoxyethoxy and ethoxyethoxy. Preferred cyanoalkyl groups are cyanomethyl and cyanoethyl. Haloalkyl itself as substituent or as part of another substituent, such as haloalkoxy or haloalkylthio, is as a rule: chloromethyl, fluoromethyl, difluoromethyl, trifluoromethyl, 2-chloroethyl, 2,2,2-trifluoroethyl, 1,1,2,2-tetrafluoroethyl, pentafluoroethyl, 1,1,2-trifluoro-2-chloroethyl, 2,2,2-trifluoro-1,1-dichloroethyl, pentachloroethyl, 3,3,3-trifluoropropyl, 2,3-dichloropropyl or 1,1,2,3,3,3-hexafluoropropyl, particularly however fluoromethyl, chloromethyl, difluoromethyl and trifluoromethyl.

The invention embraces likewise the salts which the compounds of the formula I can form with amines, alkali metal and alkaline-earth metal bases or quaternary ammonium bases.

To be emphasised among alkali metal and alkaline-earth metal hydroxides as salt formers are the hydroxides of lithium, sodium, potassium, magnesium or calcium, in particular however those of sodium and potassium.

Examples of amines suitable for forming salts are: primary, secondary and tertiary aliphatic and aromatic amines, such as methylamine, ethylamine, propylamine, i-propylamine, the four isomeric butylamines, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and i-quinoline, especially ethyl-, propyl-, diethyl- or triethylamine, but particularly iso-propylamine and diethanolamine.

Examples of quaternary ammonium bases are in general the cations of haloammonium salts, for example the tetramethylammonium cation, the trimethylbenzylammonium cation, the triethylbenzylammonium cation, the tetraethylmonium cation or the trimethylethylammonium cation, but also the ammonium cation.

Preferred compounds of the formula I according to the invention are those in which
  (a) X is the ethenylene bridge —CH=CH—; or
  (b) Z is oxygen; or
  (c) $R^1$ is $C_1$–$C_4$-alkoxycarbonyl, nitro, halogen, $C_1$–$C_4$-haloalkyl, $C_1$–$C_4$-haloalkoxy or di-$C_1$–$C_4$-alkylsulfamoyl; or
  (d) $R^2$ is hydrogen; or
  (e) $R^3$ is hydrogen; or
  (f) $R^4$ is halogen, $C_1$–$C_4$-alkoxy or $C_1$–$C_4$-alkyl; or
  (g) E is the methine bridge —CH=; or
  (h) $R^5$ is $C_1$–$C_4$-alkylcarbonyl, $C_1$–$C_4$-alkoxycarbonyl, $C_1$–$C_4$-alkoxythiocarbonyl, di-$C_1$–$C_4$-alkylcarbamoyl, di-$C_1$–$C_4$-alkylthiocarbamoyl, di-$C_1$–$C_4$-alkoxyphosphonyl, di-$C_1$–$C_4$-alkoxythiophosphonyl, N-pyrrolidinocarbonyl, N-pyrrolidinothiocarbonyl, N-morpholinothiocarbonyl, 2H-1,2,4-triazol-3-yl, 4,5-dihydrothiazol-2-yl, 1-$C_1$–$C_4$-alkyl-imidazol-2-pyridinyl or 2-pyrimidinyl.

A further preferred subgroup is formed by those compounds of the formula I in which X is the ethenylene bridge, Z is oxygen, $R^1$ is $C_1$–$C_4$-alkoxycarbonyl, nitro, halogen, $C_1$–$C_4$-haloalkyl, $C_1$–$C_4$-haloalkoxy or di-$C_1$–$C_4$-alkylsulfamoyl, and $R^2$ and $R^3$ are hydrogen.

Likewise preferred are the compounds of the formula I in which $R^4$ is halogen, $C_1$–$C_4$-alkoxy or $C_1$–$C_4$-alkyl, E is the methine bridge, and $R^5$ is $C_1$–$C_4$-alkylcarbonyl, $C_1$–$C_4$-alkoxycarbonyl, $C_1$–$C_4$-alkoxythiocarbonyl, di-$C_1$–$C_4$-alkylcarbamoyl, di-$C_1$–$C_4$-alkylthiocarbamoyl, di-$C_1$–$C_4$-alkoxyphosphonyl, di-$C_1$–$C_4$-alkoxythiophosphonyl, N-pyrrolidinocarbonyl, N-pyrrolidinothiocarbonyl, N-morpholinothiocarbonyl, 2H-1,2,4-triazol-3-yl, 4,5-dihydrothiazol-2-yl, 1-$C_1$–$C_4$-alkyl-imidazol-2-yl, 2-pyridinyl or 2-pyrimidinyl.

A particularly preferred subgroup of compounds of the formula I is formed by those in which X is the ethenylene bridge, Z is oxygen, $R^1$ is $C_1$–$C_4$-alkoxycarbonyl, nitro, halogen, $C_1$–$C_4$-haloalkoxy or di-$C_1$–$C_4$-alkylsulfamoyl, and and $R^2$ and $R^3$ are hydrogen, halogen, $C_1$–$C_4$-alkoxy or $C_1$–$C_4$-alkyl, E is the methine bridge, and $R^5$ is $C_1$–$C_4$-alkylcarbonyl, $C_1$–$C_4$-alkoxycarbonyl, $C_1$–$C_4$-alkoxythiocarbonyl, di-$C_1$–$C_4$-alkylcarbamoyl, di-$C_1$–$C_4$-alkylthiocarbamoyl, di-$C_1$–$C_4$-alkoxyphosphonyl, di-$C_1$–$C_4$-alkoxythiophosphonyl, N-pyrrolidinocarbonyl, N-pyrrolidinothiocarbonyl, N-morpholinothiocarbonyl, 2H-1,2,4-triazol-3-yl, 4,5-dihydrothiazol-2-yl, 1-$C_1$–$C_4$-alkyl-imidazol-2-yl, 2-pyridinyl or 2-pyrimidinyl.

To be mentioned as preferred individual compounds are:

N-(2-methoxycarbonylphenyl-sulfonyl)-N'-(4-methoxy-6-acetylthiomethyl-pyrimidin-2-yl)-urea, N-(2-methoxycarbonylphenyl-sulfonyl)-N'-(4-methoxy-6-methoxythiocarbonylthiomethyl-pyrimidin-2-yl)-urea, N-(2-nitrophenyl-sulfonyl)-N'-[4-methoxy-6-(4,5-dihydro-thiazol-2-yl-thiomethyl)-pyrimidin-2-yl]-urea, N-(2-methoxycarbonylphenyl-sulfonyl)-N'-(4-methoxy-6-dimethoxythiophosphonylthiomethyl-pyrimidin-2-yl)-urea, N-(2-nitrophenyl-sulfonyl)-N'-(4-methoxy-6-diethoxyphosphonylthiomethyl-pyrimidin-2-yl)-urea, and N-(2-methoxycarbonylphenyl-sulfonyl)-N'-(4-methoxy-6-di-n-butyloxythiophosphonylthiomethyl-pyrimidin-2-yl)-urea.

The compounds of the formula I are produced in general by the following methods.

One process for obtaining the compounds of the formula I comprises reacting an arylsulfonylisocyanate or arylsulfonylisothiocyanate of the formula II

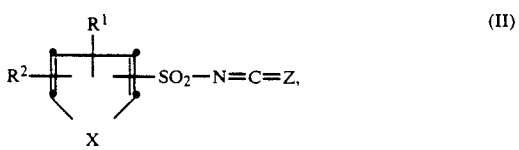

wherein $R^1$, $R^2$, X and Z have the meanings defined under the formula I, with an aminopyrimidine or aminotriazine of the formula III

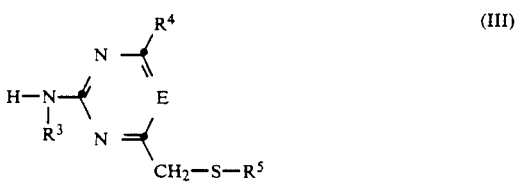

wherein $R^3$, $R^4$, $R^5$ and E have the meanings defined under the formula I.

A further process for obtaining the compounds of the formula I comprises reacting an N-arylsulfonylcarbamate of the formula IV

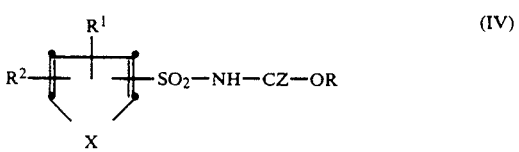

wherein $R^1$, $R^2$, X and Z have the meanings defined under the formula I, and R is phenyl, alkyl or substituted phenyl, with an aminopyrimidine or aminotriazine of the formula III.

Finally, the compounds of the formula I can be produced also by reacting a compound of the formula V

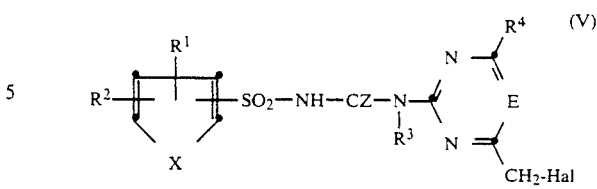

wherein $R^1$, $R^2$, $R^3$, $R^4$, X and Z have the meanings defined under the formula I, and Hal is chlorine or bromine, with a sulfur salt of the formula VI

wherein $R^5$ has the meaning defined under the formula I, and $M^\ominus$ is an alkali metal cation, alkaline-earth metal cation or ammonium cation.

The resulting ureas of the formula I can if desired be converted, by means of amines, alkali metal hydroxides or alkaline-earth metal hydroxides or quaternary ammonium bases, into addition salts. This is effected for example by reaction with the equimolar amount of a base, and removal of the solvent by evaporation.

The reactions to give compounds of the formula I are performed advantageously in aprotic, inert organic solvents. Such solvents are: hydrocarbons, such as benzene, toluene, xylene or cyclohexane, chlorinated hydrocarbons, such as methylene chloride, chloroform, carbon tetrachloride or chlorobenzene, ethers, such as diethyl ether, ethylene glycol dimethyl ether, diethylene glycol dimethyl ether, tetrahydrofuran or dioxane, nitriles, such as acetonitrile or propionitrile, amides, such as dimethylformamide, diethylformamide or N-methylpyrrolidine. The reaction temperatures are preferably between −20° and +120° C. The reactions of the coupling processes proceed in general slightly exothermically, and can be performed at room temperature. For the purpose of shortening the reaction time or for initiating the reaction, it is advantageous to apply heat for a short time up to the boiling point of the reaction mixture. The reaction times can advantageously be shortened if desired also by the addition of a few drops of a base as a reaction catalyst. Suitable bases are in particular tertiary amines, such as trimethylamine, triethylamine, quinuclidine, 1,4-diazabicyclo-(2,2,2)-octane, 1,5-diazabicyclo(4,3,0)-non-5-ene or 1,5-diazabicyclo(5,4,0)undec-7-ene. The bases used can however also be inorganic bases, such as hydrides, for example sodium or calcium hydride, hydroxides, such as sodium and potassium hydroxide, carbonates, such as sodium and potassium carbonate, or hydrogen carbonates, such as potassium and sodium bicarbonate.

The final products of the formula I can be isolated by concentration by evaporation and/or by removal of the solvent by evaporation, and purified by recrystallisation or trituration of the solid residue in solvents in which the products are not readily soluble, such as ethers, aromatic hydrocarbons or chlorinated hydrocarbons.

The intermediates of the formulae II, IV, V and VI are known, or they can be produced by methods analogous to known methods.

The aminopyrimidines and -triazines of the formula III are novel, and were specially developed and produced as intermediates for producing the active substances according to the invention. These intermediates thus form further subject matter of the present invention.

The novel aminopyrimidines and -triazines of the formula III are produced by reacting a compound of the formula VII

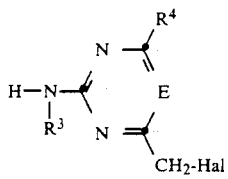

(VII)

wherein $R^3$, $R^4$ and E have the meanings defined under the formula I, and Hal is chlorine or bromine, with a sulfur salt of the formula VI.

This reaction is performed under reaction conditions which are the same as those for the reaction of the compounds V and VI.

The active substances of the formula I are stable compounds, and the handling of them requires no special precautions.

In smaller applied amounts, the compounds of the formula I are characterised by good selective growth-inhibiting and selective herbicidal properties, which render the compounds excellently suitable for use in crops of useful plants, especially in crops of cereals, cotton, soya-bean, maize and rice. Also destroyed in some cases are weeds which hitherto could be dealt with only by the use of total herbicides.

The mode of action of these active substances is unusual. Many are capable of being translocated, that is to say, they are taken up by the plant and transported to other locations, where they produce the desired effect. It is thus possible for example by surface treatment of perennial weeds to destroy them at the roots. The novel compounds of the formula I are effective in applied amounts which are very small compared with the amounts required to obtain the same effect using other herbicides and plant-growth regulators.

The compounds of the formula I have excellent properties also for regulating plant growth, especially for inhibiting plant growth. Both monocotyledons and dicotyledons are impaired in their growth.

Thus, for example, the leguminosae frequently planted as cover crops in agriculture in tropical regions can be selectively inhibited in their growth by the compounds of the formula I, the result being that soil erosion between the cultivated plants is prevented, without the cover crops being able to compete with the main cultivated crop.

A reduction of the vegetative growth enables in the case of many cultivated plants the crop density to be increased, so that higher yields for the same area of land can be achieved.

An additional factor contributing to the increase in yield with the use of growth inhibitors is that the formation of blossom and fruit benefits to a greater extent from the nutritive substances, because the vegetative growth is restricted.

With larger applied amounts of active substance, all the tested plants are impaired in their development to the extent that they wither.

The invention relates also to herbicidal and plant-growth regulating compositions containing a novel active ingredient of the formula I, and also to processes for the pre- and post-emergence controlling of weeds, and for the reduction in growth of monocotyledonous and dicotyledonous plants, particularly that of grasses, tropical cover crops and side shoots of tobacco plants.

The compounds of the formula I are used either in an unmodified form or preferably in compositions, together with auxiliaries customarily employed in formulation practice, and are thus processes, in a known manner, for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objects to be achieved and the given conditions.

The formulations, that is to say, the compositions or preparations containing the active ingredient of the formula I and optionally a solid or liquid additive, are produced in a known manner, for example by the intimate mixing and/or grinding of the active ingredients with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutylor dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones, such as cyclohexanone, strongly polar solvents, such as N-methyl-2-pyrrolidone, dimethylsulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is also possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pregranulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties. By 'tensides' are also meant mixtures of tensides.

Suitable anionic tensides are both so-called water-soluble soaps as well as water-soluble, synthetic, surface-active compounds.

Soaps which are applicable are the alkali metal, alkaline-earth metal or optionally substituted ammonium salts of higher fatty acids ($C_{10}$–$C_{22}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C atoms. Alkylarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)-ethylene oxide adduct, and phospholipides.

Suitable nonionic tensides are in particular polyglycol ether derivatives of aliphatic or cycloaliphatic alcohols, saturated or unsaturated fatty acids and alkylphenols, which can contain 3 to 10 glycol ether groups and 8 to 20 carbon atoms in the (aliphatic) hydrocarbon radical and 6 to 18 carbon atoms in the alkyl moiety of the alkylphenols.

Further suitable nonionic tensides are the watersoluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 C atoms and, as further substituents, lower, optionally halogenated alkyl, benzyl or lower hydroxyalkyl groups. The salts are preferably in the form of halides, methyl sulfates or ethyl sulfates, for example stearyltrimethylammonium chloride or benzyldi(Z-chloroethyl)ethylammonium bromide.

The tensides customarily used in formulation practice are described, inter alia, in the following publications:

"Mc Cutcheon's Detergents and Emulsifiers Annual" MC Publishing Corp., Ridgewood, N.J., 1981; H. Stache, "Tensid-Taschenbuch" (Tenside Handbook), 2nd Edition, C. Hanser Verlag, Munich, Vienna, 1981;

M and J. Ash, "Encyclopedia of Surfactants", Vol. I–III, Chemical Publishing Co., New York, 1980–1981.

The agrochemical preparations contain as a rule 0.1 to 95%, especially 0.1 to 80%, of active ingredient of the formula I, 1 to 99.9% of a solid or liquid additive, and 0 to 25%, particularly 0.1 to 25%, of a tenside.

Preferred formulations are made up in particular as follows (% = percent by weight):

| Emulsifiable concentrates | |
|---|---|
| active ingredient: | 1 to 20%, preferably 5 to 10% |
| surface active agent: | 5 to 30%, preferably 10 to 20% |
| liquid carrier | 50 to 94%, preferably 70 to 85%. |

| Dusts | |
|---|---|
| active ingredient: | 0.1 to 10%, preferably 0.2 to 1% |
| solid carrier: | 99.9 to 90%, preferably 99.9 to 99%. |
| Suspension concentrates | |
| active ingredient: | 5 to 75%, preferably 10 to 50% |
| water: | 94 to 25%, preferably 90 to 30% |
| surface-active agent: | 1 to 40%, preferably 2 to 30%. |
| Wettable powders | |
| active ingredient: | 0.5 to 90%, preferably 1 to 80% |
| surface-active agent: | 0.5 to 20%, | preferably 1 to 15% |
| solid carrier: | 5 to 95%, preferably 15 to 90%. |
| Granulates | |
| active ingredient: | 0.5 to 30%, preferably 3 to 15% |
| solid carrier: | 99.5 to 70%, preferably 97 to 85%. |

Whereas commercial products are preferably in the form of concentrated compositions, the preparations employed by the end-user are as a rule diluted. The preparations can for application be diluted down to 0.001% of active ingredient. The applied amounts are usually 0.01 to 10 kg, preferably 0.025 to 5 kg, of active ingredient per hectare.

The compositions can also contain further additives, such as stabilisers, antifoaming agents, viscosity regulators, binders and adhesives, as well as fertilisers or other active ingredients for obtaining special effects.

Production Examples

EXAMPLE P1

N-(2-Methoxycarbonylphenyl-sulfonyl)-N'-(4-methoxy-6-ethoxythiocarbonylthiomethyl-pyrimidin-2-yl)-urea (compound No. 2.4).

7.0 g of 2-amino-4-methoxy-6-ethoxythiocarbonylthiomethyl-pyrimidine and 6.5 g of 2-methoxycarbonylphenylsulfonylisocyanate are suspended in 20 ml of abs. acetonitrile, and the suspension is stirred at 20 to 25° C. for 2 hours. A clear solution is firstly formed during this time, and the final product subsequently crystallises out. To isolate the final product, the reaction mixture is cooled to 0° C. and then filtered. The yield is 9.0 g (67% of theory) of N-(2-methoxycarbonylphenyl-sulfonyl)-N'(4-methoxy-6-ethoxythiocarbonylthiomethyl-pyrimidin-2-yl)urea, m.p. 160°–162° C. (decomp.).

EXAMPLE P2

N-(2-Dimethylsulfamoylphenyl-sulfonyl)-N'-(4-methoxy-6-dimethylthiocarbamoylthiomethyl-pyrimidin-2-yl)-urea (compound No. 2.7)

A mixture of 9.3 g of N-(2-dimethylsulfamoylphenyl-sulfonyl)-N'-(4-chloromethyl-6-methoxy-pyrimidin-2-yl)urea and 3.7 g of dimethyldithiocarbamic acid sodium salt dihydrate is stirred in 100 ml of acetonitrile at 20°–25° C. for 3 hours. In further processing, the reaction mixture is diluted with 1 liter of water, and the precipitated product is separated. The yield is 10.0 g (91% of theory) of N-(2-dimethylsulfamoylphenyl-sulfonyl)-N'-(4-methoxy-6dimethylthiocarbamoylthiomethyl-pyrimidin-2-yl)-urea m.p. 181°14 183° C. (decomp.).

EXAMPLE P3

N-(Z-Nitrophenyl-sulfonyl)-N'.(4-methoxy-6-dimethyl-thiocarbamoylthiomethyl-pyrimidin-2-yl)-urea (compound No. 2.10)

7.0 g of 2-amino-4-methoxy-6-dimethylcarbamoylthio-methyl-pyrimidine and 6.2 g of 2-nitrophenyl-sulfonylisocyanate are dissolved in 80 ml of abs. acetonitrile, and the solution is stirred for 50 hours at room temperature. The product during this time precipitates partially in crystalline form and, after the reaction mixture has been cooled to 0° C., the precipitate is separated. The yield is 10.0 g (76% of theory) of N-(2-nitrophenyl-sulfonyl)-N'-(4-methoxy-6-dimethylthiocarbamoylthiomethyl-pyrimidin-2-yl)-urea, m.p. 202°–204° C. (decomp.).

EXAMPLE P4

N-(2-Methoxycarbonylphenyl-sulfonyl)-N'-[4-methoxy-6(4,5-dihydrothiazol-2-yl-thiomethyl)-pyrimidin-2-yl-urea (compound No. 2.15)

7.0 g of 2-amino-4-methoxy-6-(4,5-dihydrothiazol-2-yl)pyrimidine are suspended in 50 ml of abs. acetonitrile, and 6.6 g of 2-methoxycarbonylphenylsulfonylisocyanate are added. There is formed a clear solution with heating, and the product subsequently precipitates in crystalline form. After the reaction mixture has been stirred for 3 hours at 20°–25° C., it is cooled to 0° C. and the solid substance is separated. There is thus obtained N-(2-methoxycarbonylphenyl-sulfonyl)-N'-[4-methoxy-6-(4,5-dihydrothiazol-2-yl)-thiomethyl-pyrimidin-2-yl]-urea, m.p 135°–145° C. (decomp.).

EXAMPLE P5

N-(2-Nitrophenyl-sulfonyl)-N'-(4-methoxy-6-di-n-propyloxythiophosphonylthiomethyl-pyrimidin-2-yl)-urea (compound No. 2.23)

A mixture of 11.6 g of 2-amino-4-methoxy-di-n-propyloxythiophosphonylthiomethyl-pyrimidine and 7.5 g of 2-nitrophenylsulfonylisocyanate is stirred in 30 ml of abs. acetonitrile. The product precipitates from this mixture after a short time; the reaction mixture is stirred for a further 20 hours and is then cooled to 0° C. The yield after separation of the precipitate is 6.5 g (34% of theory) of N-(2-nitrophenyl-sulfonyl)-N'-(4-methoxy-6-di-n-propyloxythiophosphonylthiomethyl-pyrimidin-2-yl)-urea, m.p. 157°–159° C.

EXAMPLE P6

N-(2-Methoxycarbonylphenyl-sulfonyl)-N'-(4-methoxy-6-di-i-propyloxythiophosphonylthiomethyl-pyrimidin-2-yl)urea (compound No. 2.24)

A mixture of 11.0 g of 2-amino-4-methoxy-6-di-i-propyloxythiophosphonylthiomethyl-pyrimidine and 7.0 g of 2-methoxycarbonylphenylsulfonylisocyanate is stirred in 50 ml of abs. acetonitrile for 20 hours at 20°–25° C. The solvent is subsequently evaporated off in vacuo, and the oily residue is crystallised from diethyl ether. The yield is 11.0 g (60% of theory) of N-(2-methoxycarbonylphenyl-sulfonyl)-N'-(4-methoxy-6-di-i-propyloxythiophosphonylthiomethyl-pyrimidin-2-yl)-urea, m.p. 119°–123° C.

EXAMPLE P7

N-(2-Methoxycarbonylphenyl-sulfonyl)-N'-[4-methoxy-6-(pyridin-2-ylthiomethyl)-pyrimidin-2-yl]-urea (compound No. 2.36)

7.0 g of 2-amino-4-methoxy-6-(pyridin-2-ylthiomethyl)pyrimidine and 6.8 g of 2-methoxycarbonylphenyl-sulfonylisocyanate are stirred in 50 ml of abs. acetonitrile for 2 hours at 20°–25° C. The turbid solution is filtered, and the solvent evaporated off in vacuo. The residue is crystallised from dioxane to thus obtain 5.5 g (37% of theory) of N-(2-methoxycarbonylphenyl-sulfonyl)-N'-[4-methoxy-6-(pyridin-2-ylthiomethyl)-pyrimidin-2-yl]urea, which crystallises with 0.5 mol of dioxane, m.p. 175°–181° C.

EXAMPLE P8

2-Amino-4-methoxy-6-ethoxythiocarbonylthiomethylpyrimidine (compound No. 1.5)

16.0 g of potassium ethylxanthogenate and 17.4 g of 2-amino-4-chloromethyl-6-methoxy-pyrimidine are refluxed in 100 ml of ethanol for 30 minutes. After the reaction solution has cooled, it is diluted with about 1 liter of water, and the product which precipitates is separated and dried. The yield is 22.5 g (87% of theory) of 2-amino-4-methoxy-6-ethoxythiocarbonylthiomethyl-pyrimidine, m.p. 91°–93° C.

EXAMPLE P9

2-Amino-4-methoxy-6-dimethylthiocarbamoylthiomethylpyrimidine (compound No. 1.11)

18.5 g of dimethyldithiocarbamic acid sodium salt dihydrate and 17.4 g of 2-amino-4-chloromethyl-6-methoxypyrimidine are refluxed in 100 ml of ethanol for 30 minutes. After the mixture has been cooled, it is diluted with about 1 liter of water, and the product which has precipitated is separated and dried. The yield is 23.0 g (89% of theory) of 2-amino-4-methoxy-6-dimethylthiocarbamoylthiomethyl-pyrimidine, m.p. 118°–120° C.

EXAMPLE P10

2-Amino-4-methoxy-6-(4,5-dihydrothiazol-2-yl-thiomethyl)pyrimidine (compound No. 1.17)

11.9 g of 4,5-dihydro-2-mercapto-thiazole are suspended in 100 ml of methanol, and to the suspension are added 18.0 g of 30% methanolic sodium methylate solution. To the formed clear solution are subsequently added 17.4 g of 2-amino-4-chloromethyl-6-methoxypyrimidine, and refluxing is carried out for 1 hour. After the solution has cooled, it is diluted with about 1 liter of water, and the product which precipitates is separated and dried. The yield is 22.5 g (88% of theory) of 2-amino-4-methoxy-6-(4,5-dihydrothiazol-2-yl-thiomethyl)-pyrimidine, m.p. 122°–124° C.

EXAMPLE P11

2-Amino-4-methoxy 6-(pyridin-2-yl-thiomethyl)-pyrimidine (compound No. 1.18)

18 g of 30% methanolic sodium methylate solution are added to a solution of 11.1 g of 2-mercaptopyridine in 100 ml of methanol, and stirring is then maintained at 20°–25° C. for 1 hour. To this solution are added portionwise 17.4 g of 2-amino-4-chloromethyl-6-methoxypyrimidine, and the mixture is stirred at 20°–25° C. for a further 2 hours. In further processing, the mixture is diluted with 1 liter of water, and the precipitating crystalline product is separated and dried. The yield is 22.5 g (91% of theory) of 2-amino-4-methoxy-6-(pyridin-2-yl-thiomethyl)-pyrimidine, m.p. 115°–116° C.

EXAMPLE P12

2-Amino тм 4-methoxy-6-(di-n-propyloxythiophosphonylthiomethyl)-pyrimidine (compound No. 1.32)

17.9 g of 2-amino-4-chloromethyl-6-methoxy-pyrimidine and 25.5 g of dithiophosphoric acid-0,0-di-n-propyl ester potassium salt in 100 ml of ethyl methyl ketone are refluxed for 1 hour. After cooling, the solution is diluted with 1 liter of water, and extracted with 250 ml of ethyl acetate. The organic phase is dried over sodium sulfate and concentrated by evaporation. There are obtained as residue 34.0 g (97% of theory) of 2-amino-4-methoxy-6-di-n-propyloxythiophosphonylthiomethylpyrimidine in the form of a colourless viscous oil.

The intermediates and final products of the formula I which are additionally listed in the following Tables are obtained in an analogous manner.

TABLE 1

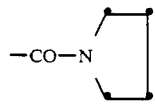

| Comp. No. | $R^3$ | E | $R^4$ | $R^5$ | Physical data |
|---|---|---|---|---|---|
| 1.1 | H | CH | $OCH_3$ | —CO—$CH_3$ | highly viscous oil |
| 1.2 | H | N | $OCH_3$ | —CO—$CH_3$ | |
| 1.3 | H | CH | $OCH_3$ | —CS—$OCH_3$ | m.p. 97–100° C. |
| 1.4 | H | N | $OCH_3$ | —CS—$OCH_3$ | |
| 1.5 | H | CH | $OCH_3$ | —CS—$OC_2H_5$ | m.p. 91–93° C. |
| 1.6 | H | N | $OCH_3$ | —CS—$OC_2H_5$ | |
| 1.7 | $CH_3$ | CH | $OCH_3$ | —CS—$OC_2H_5$ | |
| 1.8 | $CH_3$ | N | $OCH_3$ | —CS—$OC_2$—$H_5$ | |
| 1.9 | H | CH | $OCH_3$ | —CO—$N(CH_3)_2$ | m.p. 155–157° C. |
| 1.10 | H | N | $OCH_3$ | —CO—$N(CH_3)_2$ | |
| 1.11 | H | CH | $OCH_3$ | —CS—$N(CH_3)_2$ | m.p. 118–120° C. |
| 1.12 | H | N | $OCH_3$ | —CS—$N(CH_3)_2$ | |
| 1.13 | H | CH | Cl | 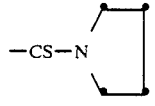 | m.p. 141–143° C. |
| 1.14 | H | CH | $OCH_3$ | 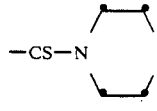 | m.p. 140–142° C. |
| 1.15 | H | CH | $OCH_3$ | 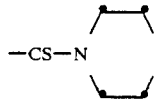 | m.p. 172–174° C. |
| 1.16 | H | N | $OCH_3$ | 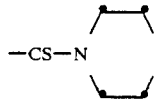 | |
| 1.17 | H | CH | $OCH_3$ | 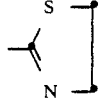 | m.p. 122–124° C. |
| 1.18 | H | CH | $OCH_3$ | 2-pyridyl | m.p. 115–116° C. |
| 1.19 | H | N | $OCH_3$ | 2-pyridyl | |
| 1.20 | $C_2H_5$ | N | $OCH_3$ | 2-pyridyl | |
| 1.21 | $C_2H_5$ | CH | $OCH_3$ | 2-pyridyl | |
| 1.22 | $C_2H_5$ | CH | $OCHF_2$ | 2-pyridyl | |
| 1.23 | H | CH | $OCHF_2$ | 2-pyridyl | |
| 1.24 | H | N | $OCHF_2$ | 2-pyridyl | |
| 1.25 | H | CH | $CH_3$ | 2-pyridyl | |
| 1.26 | H | CH | $OC_2H_5$ | 2-pyridyl | |

TABLE 1-continued

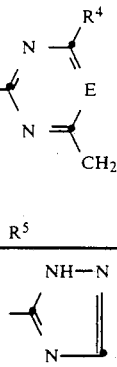

| Comp. No. | $R^3$ | E | $R^4$ | $R^5$ | Physical data |
|---|---|---|---|---|---|
| 1.27 | H | CH | OCH$_3$ | (NH—N / N heterocycle) | m.p. 188–190° C. |
| 1.28 | H | CH | OCH$_3$ | —PS(OCH$_3$)$_2$ | oil |
| 1.29 | H | CH | OCH$_3$ | —PS(OC$_2$H$_5$)$_2$ | oil |
| 1.30 | H | CH | OCH$_3$ | —PO(OC$_2$H$_5$)$_2$ | oil |
| 1.31 | H | CH | OCH$_3$ | —PS(OC$_2$H$_4$—OCH$_3$)$_2$ | oil |
| 1.32 | H | CH | OCH$_3$ | —PS(OC$_3$H$_4$-n)$_2$ | oil |
| 1.33 | H | N | CH$_3$ | —PS(OC$_3$H$_7$-n)$_2$ | oil |
| 1.34 | H | CH | OCH$_3$ | —PS(OC$_3$H$_7$-i)$_2$ | oil |
| 1.35 | H | CH | OCH$_3$ | —PS(OC$_4$H$_9$-n)$_2$ | oil |
| 1.36 | H | CH | OCH$_3$ | —PO(OC$_2$H$_5$)—SC$_3$H$_7$-n | oil |
| 1.37 | H | CH | OCH$_3$ | —PO—OC$_2$H$_5$ / S—CH—CH$_3$ / C$_3$H$_7$-n | oil |

TABLE 2

| Comp. No. | $R^1$ | $R^2$ | E | $R^4$ | $R^5$ | m.p. [°C.] |
|---|---|---|---|---|---|---|
| 2.1 | —COOCH$_3$ | H | CH | —OCH$_3$ | —CO—CH$_3$ | 175–185 (decomp.) |
| 2.2 | —COOCH$_3$ | H | CH | —OCH$_3$ | —CS—OCH$_3$ | 148–151 |
| 2.3 | —NO$_2$ | H | CH | —OCH$_3$ | —CS—OCH$_3$ | 150–155 (decomp.) |
| 2.4 | —COOCH$_3$ | H | CH | —OCH$_3$ | —CS—OC$_2$H$_5$ | 160–162 (decomp.) |
| 2.5 | —NO$_2$ | H | CH | —OCH$_3$ | —CS—OC$_2$H$_5$ | 160–162 (decomp.) |
| 2.6 | —COOCH$_3$ | H | CH | —OCH$_3$ | —CO—N(CH$_3$)$_2$ | 175–177 (decomp.) |
| 2.7 | —SO$_2$—N(CH$_3$)$_2$ | H | CH | —OCH$_3$ | —CS—N(CH$_3$)$_2$ | 181–183 (decomp.) |
| 2.8 | —CF$_3$ | H | CH | —OCH$_3$ | —CS—N(CH$_3$)$_2$ | 202–204 (decomp.) |
| 2.9 | —COOCH$_3$ | H | CH | —OCH$_3$ | —CS—N(CH$_3$)$_2$ | 185–187 (decomp.) |
| 2.10 | —NO$_2$ | H | CH | —OCH$_3$ | —CS—N(CH$_3$)$_2$ | 202–204 (decomp.) |
| 2.11 | —COOCH$_3$ | H | CH | —OCH$_3$ | —CS—N (pyrrolidinyl) | 197–199 (decomp.) |
| 2.12 | —CF$_3$ | H | CH | —OCH$_3$ | —CS—N (pyrrolidinyl) | 217–219 (decomp.) |
| 2.13 | —COOCH$_3$ | H | CH | —OCH$_3$ | —CS—N (morpholinyl) | 185–187 (decomp.) |

TABLE 2-continued

Structure: $R^2$-substituted phenyl-$SO_2$-NH-CO-NH-C(=N-C(R^4)=E-C(CH_2-S-R^5)=N-)$ with $R^1$ on phenyl

| Comp. No. | $R^1$ | $R^2$ | E | $R^4$ | $R^5$ | m.p. [°C.] |
|---|---|---|---|---|---|---|
| 2.14 | —COOCH$_3$ | H | CH | —Cl | —CO—N(pyrrolidinyl) | 175–177 (decomp.) |
| 2.15 | —COOCH$_3$ | H | CH | —OCH$_3$ | 2-methyl-thiazolinyl (N=C(CH_3)-S-CH_2-CH_2-) | 135–145 (decomp.) |
| 2.16 | —NO$_2$ | H | CH | —OCH$_3$ | 2-methyl-thiazolinyl | 160–163 (decomp.) |
| 2.17 | —OCHF$_2$ | H | CH | —Cl | —CO—N(pyrrolidinyl) | 150–155 (decomp.) |
| 2.18 | —Cl | H | CH | —Cl | —CO—N(pyrrolidinyl) | 139–142 (decomp.) |
| 2.19 | —NO$_2$ | H | CH | —Cl | —CO—N(pyrrolidinyl) | 145–160 (decomp.) |
| 2.20 | —OCHF$_2$ | H | CH | —OCH$_3$ | 3-methyl-1H-1,2,4-triazol-5-yl | 99–101 (decomp.) |
| 2.21 | —NO$_2$ | H | N | —CH$_3$ | 2-methyl-thiazolinyl | |
| 2.22 | —COOCH$_3$ | H | CH | —OCH$_3$ | —P(=S)(OC$_3$H$_7$-n)$_2$ | 98–101 |
| 2.23 | —NO$_2$ | H | CH | —OCH$_3$ | —P(=S)(OC$_3$H$_7$-n)$_2$ | 157–159 |
| 2.24 | —COOCH$_3$ | H | CH | —OCH$_3$ | —P(=S)(OC$_3$H$_7$-i)$_2$ | 119–123 |

TABLE 2-continued

[Structure: R²–(phenyl with R¹)–SO₂–NH–CO–NH–C(=N–R⁴)(–E=)–N=CH–CH₂–S–R⁵ ring system]

| Comp. No. | R¹ | R² | E | R⁴ | R⁵ | m.p. [°C.] |
|---|---|---|---|---|---|---|
| 2.25 | NO₂ | H | CH | —OCH₃ | —PS(OC₃H₇-i)₂ | 182–184 (decomp.) |
| 2.26 | —COOCH₃ | H | CH | —OCH₃ | —PS(OC₄H₉-n)₂ | 106–108 |
| 2.27 | —NO₂ | H | CH | —OCH₃ | —PS(OC₄H₉-n)₂ | 112–114 |
| 2.28 | —Cl | 3-Cl | CH | —OCH₃ | —CS—N(CH₃)₂ | 204–206 (decomp.) |
| 2.29 | —Cl | H | CH | —OCH₃ | —PS(OC₂H₅)₂ | 132–135 |
| 2.30 | —Cl | 3-Cl | CH | —OCH₃ | [thiazoline ring S/N] | 168–169 (decomp.) |
| 2.31 | —Cl | 6-Cl | CH | —OCH₃ | [thiazoline ring S/N] | 182–184 (decomp.) |
| 2.32 | —Cl | 3-Cl | CH | —OCH₃ | —PS(OC₂H₅)₂ | 136–138 |
| 2.33 | —CF₃ | H | CH | —OCH₃ | [N/S ring] | 145–148 |
| 2.34 | —OCH₃ | H | CH | —OCH₃ | [N/S ring] | 162–164 (decomp.) |
| 2.35 | —OCH₃ | H | CH | —OCH₃ | [N—N(CH₃) ring] | 90–92 (decomp.) |
| 2.36 | —COOCH₃ | H | CH | —OCH₃ | 2-pyridinyl | 182–184 (decomp.) |
| 2.37 | —OCH₃ | H | CH | —OCH₃ | 2-pyrimidinyl | 197–199 (decomp.) |
| 2.38 | —COOCH₃ | H | CH | —OCH₃ | —PS(OCH₃)₂ | 152–154 (decomp.) |
| 2.39 | —NO₂ | H | CH | —OCH₃ | —PS(OCH₃)₂ | 120–125 (decomp.) |
| 2.40 | —COOCH₃ | H | CH | —OCH₃ | —PS(OC₂H₅)₂ | 128–130 |
| 2.41 | —NO₂ | H | CH | —OCH₃ | —PS(OC₂H₅)₂ | 168–170 |
| 2.42 | —COOCH₃ | H | CH | —OCH₃ | —PS(O—C₂H₄—OCH₃)₂ | 69–73 |

TABLE 2-continued

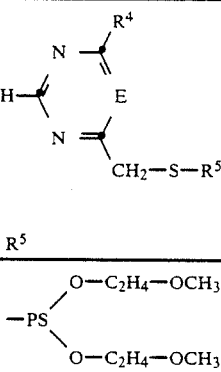

| Comp. No. | R¹ | R² | E | R⁴ | R⁵ | m.p. [°C.] |
|---|---|---|---|---|---|---|
| 2.43 | $-NO_2$ | H | CH | $-OCH_3$ | $-PS\begin{matrix}O-C_2H_4-OCH_3\\O-C_2H_4-OCH_3\end{matrix}$ | 117–120 |
| 2.44 | $-NO_2$ | H | CH | $-OCH_3$ | $-PO-(OC_2H_5)_2$ | 154–159 |
| 2.45 | $-NO_2$ | H | CH | $-OCH_3$ | $-PO\begin{matrix}O-C_2H_5\\S-C_3H_7\text{-}n\end{matrix}$ | 136–139 (decomp.) |
| 2.46 | $-COOCH_3$ | H | CH | $-OCH_3$ | $-PO\begin{matrix}OC_2H_5\\S-CH\begin{matrix}CH_3\\C_3H_7\text{-}n\end{matrix}\end{matrix}$ | oil |
| 2.47 | $-NO_2$ | H | CH | $-OCH_3$ | $-PO\begin{matrix}OC_2H_5\\S-CH\begin{matrix}CH_3\\C_3H_7\text{-}n\end{matrix}\end{matrix}$ | oil |
| 2.48 | $-OCH_3$ | H | CH | $-OCH_3$ | $-CS-OC_2H_5$ | |
| 2.49 | $-CF_3$ | H | N | $-OCH_3$ | 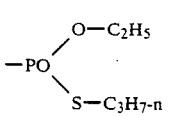 | |
| 2.50 | $-OCH_3$ | H | N | $-OCH_3$ | 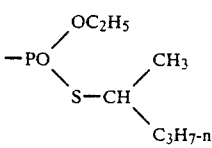 | |
| 2.51 | $-OCH_3$ | H | N | $-OCH_3$ | 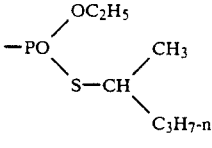 | |
| 2.52 | $-COOCH_3$ | H | N | $-OCH_3$ | 2-pyridinyl | |
| 2.53 | $-OCH_3$ | H | N | $-OCH_3$ | 2-pyrimidinyl | |
| 2.54 | $-COOCH_3$ | H | N | $-OCH_3$ | $-PS(OCH_3)_2$ | |
| 2.55 | $-NO_2$ | H | N | $-OCH_3$ | $-PS(OCH_3)_2$ | |
| 2.56 | $-COOCH_3$ | H | N | $-OCH_3$ | $-PS(OC_2H_3)_2$ | |
| 2.57 | $-NO_2$ | H | N | $-OCH_3$ | $-PS(OC_2H_5)_2$ | 160–163 (decomp.) |
| 2.58 | $-COOCH_3$ | H | N | $-OCH_3$ | $-PS\begin{matrix}O-C_2H_4-OCH_3\\O-C_2H_4-OCH_3\end{matrix}$ | |
| 2.59 | $-NO_2$ | H | N | $-OCH_3$ | $-PS\begin{matrix}O-C_2H_4-OCH_3\\O-C_2H_4-OCH_3\end{matrix}$ | |

TABLE 2-continued

[Structure: R²-substituted phenyl-SO₂-NH-CO-NH-C(=N-R⁴)(E)-CH₂-S-R⁵ with R¹ on phenyl]

| Comp. No. | R¹ | R² | E | R⁴ | R⁵ | m.p. [°C.] |
|---|---|---|---|---|---|---|
| 2.60 | —NO₂ | H | N | —OCH₃ | —PO(OC₂H₅)₂ | |
| 2.61 | —NO₂ | H | N | —OCH₃ | —PO(O—C₂H₅)(S—C₃H₇-n) | |
| 2.62 | —COOCH₃ | H | N | —OCH₃ | —PO(OC₂H₅)(S—CH(CH₃)C₃H₇-n) | |
| 2.63 | —NO₂ | H | N | —OCH₃ | —PO(OC₂H₅)(S—CH(CH₃)C₃H₇-n) | |
| 2.64 | —OCH₃ | —OCH₃ | N | —OCH₃ | —CS—OC₂H₅ | |
| 2.65 | —OCHF₂ | H | N | —Cl | —CO—N(pyrrolidinyl) | |
| 2.66 | —Cl | H | N | —Cl | —CO—N(pyrrolidinyl) | |
| 2.67 | —NO₂ | H | N | —Cl | —CO—N(pyrrolidinyl) | |
| 2.68 | —OCHF₂ | H | N | —OCH₃ | imidazolyl-NH | |
| 2.69 | —COOCH₃ | H | N | —OCH₃ | —PS(OC₃H₇-n)(O—C₃H₇-n) | |
| 2.70 | —NO₂ | H | N | —OCH₃ | —PS(OC₃H₇-n)(OC₃H₇-n) | |
| 2.71 | —COOCH₃ | H | N | —OCH₃ | —PS(OC₃H₇-i)(OC₃H₇-i) | |

TABLE 2-continued

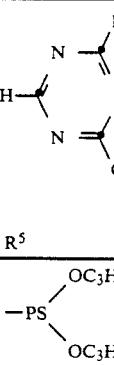

| Comp. No. | R¹ | R² | E | R⁴ | R⁵ | m.p. [°C.] |
|---|---|---|---|---|---|---|
| 2.72 | —NO₂ | H | N | —OCH₃ | —PS(OC₃H₇-i)₂ | |
| 2.73 | —COOCH₃ | H | N | —OCH₃ | —PS(OC₄H₉-n)₂ | |
| 2.74 | —NO₂ | H | N | —OCH₃ | —PS(OC₄H₉-n)₂ | |
| 2.75 | —Cl | 3-Cl | N | —OCH₃ | —CS—N(CH₃)₂ | |
| 2.76 | —Cl | H | N | —OCH₃ | —PS(OC₂H₅)₂ | |
| 2.77 | —Cl | 3-Cl | N | —OCH₃ | (thiazoline ring) | |
| 2.78 | —Cl | 6-Cl | N | —OCH₃ | (thiazoline ring) | |
| 2.79 | —Cl | 3-Cl | N | —OCH₃ | —PS(OC₂H₅)₂ | |
| 2.80 | —COOCH₃ | H | N | —OCH₃ | —CO—CH₃ | |
| 2.81 | —COOCH₃ | H | N | —OCH₃ | —CS—OCH₃ | |
| 2.82 | —NO₂ | H | N | —OCH₃ | —CS—OCH₃ | |
| 2.83 | —COOCH₃ | H | N | —OCH₃ | —CS—OC₂H₅ | |
| 2.84 | —NO₂ | H | N | —OCH₃ | —CS—OC₂H₅ | |
| 2.85 | —COOCH₃ | H | N | —OCH₃ | —CO—N(CH₃)₂ | |
| 2.86 | —SO₂—N(CH₃)₂ | H | N | —OCH₃ | —CS—N(CH₃)₂ | |
| 2.87 | —CF₃ | H | N | —OCH₃ | —CS—N(CH₃)₂ | |
| 2.88 | —COOCH₃ | H | N | —OCH₃ | —CS—N(CH₃)₂ | |
| 2.89 | —NO₂ | H | N | —OCH₃ | —CS—N(CH₃)₂ | |
| 2.90 | —COOCH₃ | H | N | —OCH₃ | —CS—N(pyrrolidinyl) | |
| 2.91 | —CF₃ | H | N | —OCH₃ | —CS—N(pyrrolidinyl) | |
| 2.92 | —COOCH₃ | H | N | —OCH₃ | —CS—N(morpholinyl) | |
| 2.93 | —COOCH₃ | H | N | —Cl | —CO—N(pyrrolidinyl) | |

TABLE 2-continued

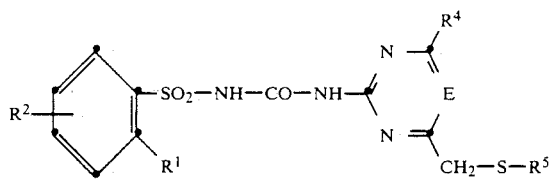

| Comp. No. | R¹ | R² | E | R⁴ | R⁵ | m.p. [°C.] |
|---|---|---|---|---|---|---|
| 2.94 | —COOCH₃ | H | N | —OCH₃ | thiazolyl-CH₂ | |
| 2.95 | —NO₂ | H | N | —OCH₃ | thiazolyl-CH₂ | |
| 2.96 | —CF₃ | H | N | —CH₃ | thiazolyl-CH₂ | |
| 2.97 | —OCH₃ | H | N | —CH₃ | thiazolyl-CH₂ | |
| 2.98 | —OCH₃ | H | N | —CH₃ | N-methylimidazolyl-CH₂ | |
| 2.99 | —COOCH₃ | H | N | —CH₃ | 2-pyridinyl | |
| 2.100 | —OCH₃ | H | N | —CH₃ | 2-pyrimidinyl | |
| 2.101 | —COOCH₃ | H | N | —CH₃ | —PS(OCH₃)₂ | |
| 2.102 | —NO₂ | H | N | —CH₃ | —PS(OCH₃)₂ | |
| 2.103 | —COOCH₃ | H | N | —CH₃ | —PS(OC₂H₅)₂ | |
| 2.104 | —NO₂ | H | N | —CH₃ | —PS(OC₂H₅)₂ | |
| 2.105 | —COOCH₃ | H | N | —CH₃ | —PS(O—C₂H₄—OCH₃)₂ | |
| 2.106 | —NO₂ | H | N | —CH₃ | —PS(O—C₂H₄—OCH₃)₂ | |
| 2.107 | —NO₂ | H | N | —CH₃ | —PO(OC₂H₅)₂ | |
| 2.108 | —NO₂ | H | N | —CH₃ | —PO(O—C₂H₅)(S—C₃H₇-n) | |
| 2.109 | —COOCH₃ | H | N | —CH₄ | —PO(OC₂H₅)(S—CH(CH₃)(C₃H₇-n)) | |

TABLE 2-continued
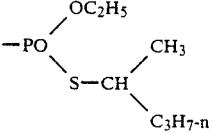
| Comp. No. | R¹ | R² | E | R⁴ | R⁵ | m.p. [°C.] |
|---|---|---|---|---|---|---|
| 2.110 | —NO₂ | H | N | —CH₃ | 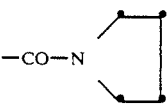 | |
| 2.111 | OCH₃ | OCH₃ | N | —CH₃ | —CS—OC₂H₅ | |
| 2.112 | —OCHF₂ | H | N | —C₂H₅ | 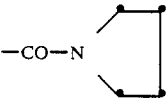 | |
| 1.113 | —Cl | H | N | —C₂H₅ | 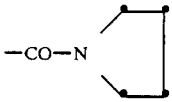 | |
| 2.114 | —NO₂ | H | N | —C₂H₅ | 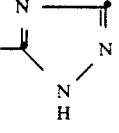 | |
| 2.115 | —OCHF₂ | H | N | —CH₃ | 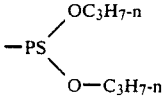 | |
| 2.116 | —COOCH₃ | H | N | —CH₃ | 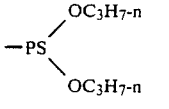 | |
| 2.117 | —NO₂ | H | N | —CH₃ | 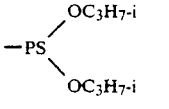 | |
| 2.118 | —COOCH₃ | H | N | —CH₃ | 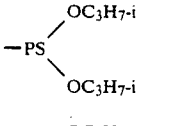 | |
| 2.119 | —NO₂ | H | N | —CH₃ | 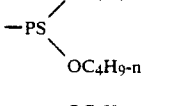 | |
| 2.120 | COOCH₃ | H | N | —CH₃ | 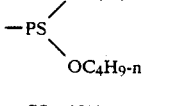 | |
| 2.121 | —NO₂ | H | N | —CH₃ | —PS(OC₄H₉-n)(OC₄H₉-n) | |
| 2.122 | —Cl | 3-Cl | N | —CH₃ | —CS—N(CH₃)₂ | |

TABLE 2-continued

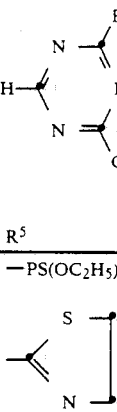

| Comp. No. | R¹ | R² | E | R⁴ | R⁵ | m.p. [°C.] |
|---|---|---|---|---|---|---|
| 2.123 | —Cl | H | N | —CH₃ | —PS(OC₂H₅)₂ | |
| 2.124 | —Cl | 3-Cl | N | —CH₃ | 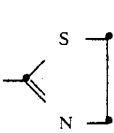 | |
| 2.125 | —Cl | 6-Cl | N | —CH₃ | 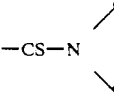 | |
| 2.126 | —Cl | 3-Cl | N | —CH₃ | —PS(OC₂H₅)₂ | |
| 2.127 | —COOCH₃ | H | N | —CH₃ | —CO—CH₃ | |
| 2.128 | —COOCH₃ | H | N | —CH₃ | —CS—OCH₃ | |
| 2.129 | —NO₂ | H | N | —CH₃ | —CS—OCH₃ | |
| 2.130 | —COOCH₃ | H | N | —CH₃ | —CS—OC₂H₅ | |
| 2.131 | —NO₂ | H | N | —CH₃ | —CS—OC₂H₅ | |
| 2.132 | —COOCH₃ | H | N | —CH₃ | —CO—N(CH₃)₂ | |
| 2.133 | —SO₂—N(CH₃)₂ | H | N | —CH₃ | —CS—N(CH₃)₂ | |
| 2.134 | —CF₃ | H | N | —CH₃ | —CS—N(CH₃)₂ | |
| 2.135 | —COOCH₃ | H | N | —CH₃ | —CS—N(CH₃)₂ | |
| 2.136 | —NO₂ | H | N | —CH₃ | —CS—N(CH₃)₂ | |
| 2.137 | —COOCH₃ | H | N | —CH₃ | 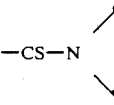 | |
| 2.138 | —CF₃ | H | N | —CH₃ | 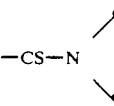 | |
| 2.139 | —COOCH₃ | H | N | —CH₃ | 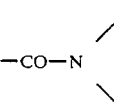 | |
| 2.140 | —COOCH₃ | H | N | —OCHF₂ | 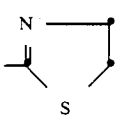 | |
| 2.141 | —COOCH₃ | H | N | —CH₃ | 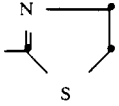 | |
| 2.142 | —O—CCl=CHCl | H | CH | —OCH₃ | —CS—N(CH₃)₂ | 179–181 (decomp.) |
| 2.143 | —OCHF₂ | H | CH | Cl | —CS—N(CH₃)₂ | 171–173 (decomp.) |
| 2.144 | —OCHF₂ | H | CH | Cl | 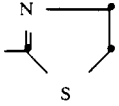 | 148–150 (decomp.) |
| 2.145 | —O—SO₂CH₃ | H | CH | —OCH₃ | —CS—N(CH₃)₂ | 173–177 (decomp.) |
| 2.146 | —OCH₂CH₂Cl | H | CH | —OCH₃ | —CS—N(CH₃)₂ | 187–190 (decomp.) |

TABLE 2-continued

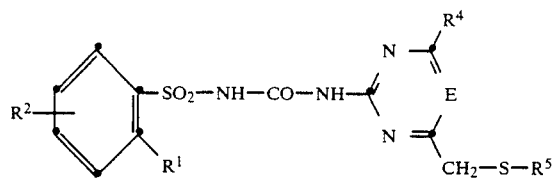

| Comp. No. | R¹ | R² | E | R⁴ | R⁵ | m.p. [°C.] |
|---|---|---|---|---|---|---|
| 2.147 | $CF_3$ | H | CH | $-OCH_3$ | $-PS\begin{smallmatrix}OCH_3\\NH-CH(CH_3)_2\end{smallmatrix}$ | 135–138 |
| 2.148 | Cl | H | N | $-OCH_3$ | $-CS-N(CH_3)_2$ | 167–169 (decomp.) |
| 2.149 | Cl | H | N | $-OCH_3$ | (thiazoline ring) | 154–156 (decomp.) |

TABLE 3 pyridine-$SO_2-NH-CO-NH-$ triazine with $R^3$, E, $R^4$, $CH_2-S-R^5$

| Comp. No. | R³ | E | R⁴ | R⁵ |
|---|---|---|---|---|
| 3.1 | Cl | CH | $OCH_3$ | $-CS-OCH_3$ |
| 3.2 | Cl | CH | $OCH_3$ | $-CS-OC_2H_5$ |
| 3.3 | Cl | CH | $OCH_3$ | $-CS-N(CH_3)_2$ |
| 3.4 | Cl | CH | $OCH_3$ | $-CS-N(C_2H_5)_2$ |
| 3.5 | Cl | CH | $OCH_3$ | (thiazoline) |
| 3.6 | Cl | CH | $OCH_3$ | $-PS(-OC_2H_5)_2$ |
| 3.7 | Cl | CH | $OCH_3$ | $-PO(OC_2H_5)_2$ |
| 3.8 | Cl | CH | $OCH_3$ | $-PS(OC_3H_7-n)_2$ |
| 3.9 | $CH_3$ | CH | Cl | $-CS-OC_2H_5$ |
| 3.10 | $CH_3$ | CH | $OC_2H_5$ | $-CS-OC_2H_5$ |
| 3.11 | $CH_3$ | CH | $CH_3$ | $-CS-OC_2H_5$ |
| 3.12 | $CH_3$ | CH | $OC_3H_7-i$ | $-CS-OC_2H_5$ |
| 3.13 | Cl | N | $OCH_3$ | $-CS-OCH_3$ |
| 3.14 | Cl | N | $CH_3$ | $-CS-OCH_3$ |
| 3.15 | $-COOCH_3$ | CH | $OCH_3$ | $-CS-OCH_3$ |
| 3.16 | $-COOCH_3$ | N | $CH_3$ | $-CS-OCH_3$ |
| 3.17 | $-COOCH_3$ | N | $OCH_3$ | $-CS-OCH_3$ |
| 3.18 | Cl | N | Cl | $-CS-OCH_3$ |
| 3.19 | Cl | N | $CH_3$ | $-CS-N(CH_3)_2$ |
| 3.20 | Cl | N | $CH_3$ | $-CS-OC_2H_5$ |
| 3.21 | Cl | N | $CH_3$ | $-PS(OC_2H_5)_2$ |
| 3.22 | Cl | N | $CH_3$ | $-PO(OCH_3)_2$ |
| 3.23 | Cl | N | $CH_3$ | $-PS(OC_3H_7-n)_2$ |
| 3.24 | Cl | N | $CH_3$ | (thiazoline) |

TABLE 4

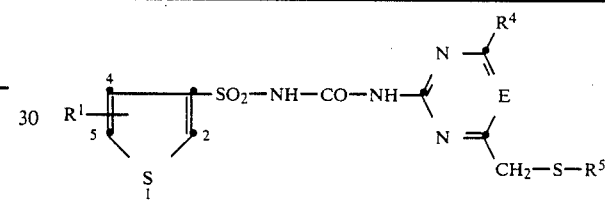

| Comp. No. | R¹ | E | R⁴ | R⁵ |
|---|---|---|---|---|
| 4.1 | 2-$COOCH_3$ | CH | $OCH_3$ | $-CS-OCH_3$ |
| 4.2 | 2-$COOCH_3$ | CH | $OCH_3$ | $-CS-OC_2H_5$ |
| 4.3 | 2-$COOCH_3$ | CH | $OCH_3$ | $-CS-N(CH_3)_2$ |
| 4.4 | 2-$COOCH_3$ | CH | $OCH_3$ | $-CS-N(C_2H_5)_2$ |
| 4.5 | 2-$COOCH_3$ | CH | $OCH_3$ | (thiazoline) |
| 4.6 | 2-$COOCH_3$ | CH | $OCH_3$ | $-PS(-OC_2H_5)_2$ |
| 4.7 | 2-$COOCH_3$ | CH | $OCH_3$ | $-PO(OC_2H_5)_2$ |
| 4.8 | 2-$COOCH_3$ | CH | $OCH_3$ | $-PS(OC_3H_7-n)_2$ |
| 4.9 | 2-$COOCH_3$ | CH | Cl | $-CS-OC_2H_5$ |
| 4.10 | 2-$COOCH_3$ | CH | $OC_2H_5$ | $-CS-OC_2H_5$ |
| 4.11 | 2-$COOCH_3$ | CH | $CH_3$ | $-CS-OC_2H_5$ |
| 4.12 | 2-$COOCH_3$ | CH | $OC_3H_7-i$ | $-CS-OC_2H_5$ |
| 4.13 | 2-$COOCH_3$ | N | $OCH_3$ | $-CS-OCH_3$ |
| 4.14 | 2-$COOCH_3$ | N | $CH_3$ | $-CS-OCH_3$ |
| 4.15 | 2-$COOCH_3$ | CH | $OCH_3$ | $-CS-OCH_3$ |
| 4.16 | 2-$COOCH_3$ | N | $CH_3$ | $-CS-OCH_3$ |
| 4.17 | 2-$COOCH_3$ | N | $OCH_3$ | $-CS-OCH_3$ |
| 4.18 | 2-$COOCH_3$ | N | Cl | $-CS-OCH_3$ |
| 4.19 | 2-$COOCH_3$ | N | $CH_3$ | $-CS-N(CH_3)_2$ |
| 4.20 | 2-$COOCH_3$ | N | $CH_3$ | $-CS-OC_2H_5$ |
| 4.21 | 2-$COOCH_3$ | N | $CH_3$ | $-PS(OC_2H_5)_2$ |
| 4.22 | 2-$COOCH_3$ | N | $CH_3$ | $-PO(OCH_3)_2$ |
| 4.23 | 2-$COOCH_3$ | N | $CH_3$ | $-PS(OC_3H_7-n)_2$ |
| 4.24 | 2-$COOCH_3$ | N | $CH_3$ | (thiazoline) |
| 4.25 | 4-$COOCH_3$ | CH | $OCH_3$ | $-CS-OCH_3$ |
| 4.26 | 4-$COOCH_3$ | CH | $OCH_3$ | $-CS-OC_2H_5$ |
| 4.27 | 4-$COOCH_3$ | CH | $OCH_3$ | $-CS-N(CH_3)_2$ |
| 4.28 | 4-$COOCH_3$ | CH | $OCH_3$ | $-CS-N(C_3H_5)_2$ |

TABLE 4-continued

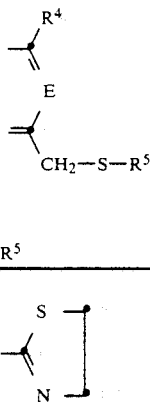

| Comp. No. | R¹ | E | R⁴ | R⁵ |
|---|---|---|---|---|
| 4.29 | 4-COOCH$_3$ | CH | OCH$_3$ | 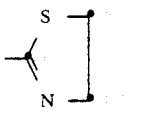 |
| 4.30 | 4-COOCH$_3$ | CH | OCH$_3$ | —PS(—OC$_2$H$_5$)$_2$ |
| 4.31 | 4-COOCH$_3$ | CH | OCH$_3$ | —PO(OC$_2$H$_5$)$_2$ |
| 4.32 | 4-COOCH$_3$ | CH | OCH$_3$ | —PS(OC$_3$H$_7$-n)$_2$ |
| 4.33 | 4-COOCH$_3$ | CH | Cl | —CS—OC$_2$H$_5$ |
| 4.34 | 3-COOCH$_3$ | CH | OC$_2$H$_5$ | —CS—OC$_2$H$_5$ |
| 4.35 | 4-COOCH$_3$ | CH | CH$_3$ | —CS—OC$_2$H$_5$ |
| 4.36 | 4-COOCH$_3$ | CH | OC$_3$H$_7$-i | —CS—OC$_2$H$_5$ |
| 4.37 | 4-COOCH$_3$ | N | OCH$_3$ | —CS—OCH$_3$ |
| 4.38 | 4-COOCH$_3$ | N | CH$_3$ | —CS—OCH$_3$ |
| 4.39 | 4-COOCH$_3$ | CH | OCH$_3$ | —CS—OCH$_3$ |
| 4.40 | 4-COOCH$_3$ | N | CH$_3$ | —CS—OCH$_3$ |
| 4.41 | 4-COOCH$_3$ | N | OCH$_3$ | —CS—OCH$_3$ |
| 4.42 | 4-COOCH$_3$ | N | Cl | —CS—OCH$_3$ |
| 4.43 | 4-COOCH$_3$ | N | CH$_3$ | —CS—N(CH$_3$)$_2$ |
| 4.44 | 4-COOCH$_3$ | N | CH$_3$ | —CS—OC$_2$H$_5$ |
| 4.45 | 4-COOCH$_3$ | N | CH$_3$ | —PS(OC$_2$H$_5$)$_2$ |
| 4.46 | 4-COOCH$_3$ | N | CH$_3$ | —PO(OCH$_3$)$_2$ |
| 4.47 | 4-COOCH$_3$ | N | CH$_3$ | —PS(OC$_3$H$_7$-n)$_2$ |
| 4.48 | 4-COOCH$_3$ | N | CH$_3$ | 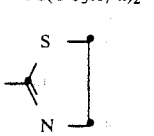 |

Formulation Examples

EXAMPLE F1

Formulation Examples for active ingredients of the formula I (% = per cent by weight)

| (a) Wettable powder | (a) | (b) | (c) |
|---|---|---|---|
| active ingredient | 20% | 60% | 0.5% |
| sodium lignin sulfonate | 5% | 5% | 5% |
| sodium lauryl sulfate | 3% | — | — |
| sodium diisobutylnaphthalene sulfonate | — | 6% | 6% |
| octylphenolpolyethylene glycol ether (7–8 mols of ethylene oxide) | — | 2% | 2% |
| highly dispersed silicic acid | 5% | 27% | 27% |
| kaolin | 67% | — | — |
| sodium chloride | — | — | 59.5% |

The active ingredient is well mixed with the additives and ground in a suitable mill. There are obtained wettable powders which can be diluted with water to give suspensions of the concentration desired.

| (b) Emulsion concentrate | (a) | (b) |
|---|---|---|
| active ingredient | 10% | 1% |
| octylphenolpolyethylene glycol ether (4–5 mols of ethylene oxide) | 3% | 3% |
| calcium dodecyl benzene sulfonate | 3% | 3% |
| castor oil polyglycol ether (36 mols of ethylene oxide) | 4% | 4% |
| cyclohexanone | 30% | 10% |
| xylene mixture | 50% | 79% |

Emulsions of the concentration desired can be obtained from this concentrate by dilution with water.

| (c) Dust | (a) | (b) |
|---|---|---|
| active ingredient | 0.1% | 1% |
| talcum | 99.9% | — |
| kaolin | — | 99% |

Dusts ready for use are obtained by mixing the active-ingredient with the carriers, and grinding the mixture in a suitable mill.

| (d) Extruder granulate | (a) | (b) |
|---|---|---|
| active ingredient | 10% | 1% |
| sodium lignin sulfonate | 2% | 2% |
| carboxymethylcellulose | 1% | 1% |
| kaolin | 87% | 96% |

The active ingredient is mixed with the additives, and the mixture is then ground and moistened with water. It is extruded and subsequently dried in a stream of air.

| (e) Coated granuate | | |
|---|---|---|
| active ingredient | | 3% |
| polyethylene glycol (MW 200) | | 3% |
| kaolin | | 94% |

The finely ground active ingredient is uniformuly applied, in a mixer, to the kaolin moistened with polyethylene glycol. Non-dusty coated granulates are obtained in this manner.

| (f) Suspension concentrate | (a) | (b) |
|---|---|---|
| active ingredient | 40% | 5% |
| ethylene glycol | 10% | 10% |
| nonylphenolpolyethylene glycol ether (15 mols of ethylene oxide) | 6% | 1% |
| sodium lignin sulfonate | 10% | 5% |
| carboxymethylcellulose | 1% | 1% |
| 37% aqueous formaldehyde solution | 0.2% | 0.2% |
| silicone oil in the form of a 75% aqueous emulsion | 0.8% | 0.8% |
| water | 32% | 77% |

The finely ground active ingredient is intimately mixed with the additives. There is thus obtained a suspension concentrate from which can be produced, by dilution with water, suspensions of the concentration required.

| (g) Salt solution | | |
|---|---|---|
| active ingredient | | 5% |
| isopropylamine | | 1% |
| octylphenolpolyethylene glycol ether (78 mols of ethylene oxide) | | 3% |
| water | | 91% |

Biological Examples

EXAMPLE B1

Herbicidal action before emergence of the plants

Plastics pots are filled with expanded vermiculite (density: 0.135 g/cm$^3$, water-absorption capacity: 0.565 1/1). After saturation of the non-adsorptive vermiculite with and aqueous active-ingredient emulsion in deionised water, which contains the active ingredient at a concentration of 70.8 ppm, seeds of the following plants are sown on the surface: *Nasturtium officinalis, Agrostis tenuis, Stellaria media* and *Digitaria sanguinalis*. The test vessels are subsequently kept in a climatic chamber at 20° C. with an illumination of about 20 k lux and a relative humidity of 70%. During the germination phase of 4 to 5 days, the pots are covered over with light-permeable material in order to raise the local air humidity and watered with deionised water. After the 5th day, 0.5% of a commercial liquid fertiliser (®Greenzit, ex Ciba-Geigy) is added to the water. The test is evaluated 12 days after sowing, and the effect on the test plants assessed according to the following scale of ratings:

| |
|---|
| 1 plants have not germinated |
| 2-3 very strong action |
| 4-6 medium action |
| 7-8 weak action |
| 9 no action (as untreated control plants). |

Pre-emergence action

Concentration of the active-ingredient emulsion: 70.8 ppm

| Active ingredient No | Test plant | | | |
|---|---|---|---|---|
| | Nasturtium | Stellaria | Agrostis | Digitaria |
| 2.1 | 2 | 2 | 1 | 1 |
| 2.2 | 1 | 1 | 1 | 1 |
| 2.3 | 2 | 1 | 1 | 2 |
| 2.4 | 1 | 2 | 1 | 2 |
| 2.5 | 2 | 1 | 1 | 1 |
| 2.6 | 2 | 1 | 2 | 2 |
| 2.7 | 2 | 1 | 1 | 2 |
| 2.8 | 1 | 2 | 1 | 2 |
| 2.9 | 2 | 1 | 2 | 2 |
| 2.10 | 2 | 1 | 1 | 1 |
| 2.11 | 2 | 2 | 1 | 2 |
| 2.13 | 2 | 1 | 1 | 2 |
| 2.14 | 2 | 2 | 2 | 3 |
| 2.15 | 1 | 2 | 1 | 2 |
| 2.16 | 1 | 1 | 1 | 1 |
| 2.17 | 3 | 2 | 2 | 5 |
| 2.19 | 1 | 1 | 1 | 2 |
| 2.20 | 1 | 1 | 1 | 2 |
| 2.22 | 2 | 1 | 1 | 1 |
| 2.23 | 2 | 2 | 1 | 2 |
| 2.24 | 2 | 1 | 2 | 2 |
| 2.25 | 2 | 2 | 1 | 2 |
| 2.26 | 1 | 1 | 1 | 1 |
| 2.27 | 1 | 1 | 1 | 2 |
| 2.28 | 2 | 2 | 2 | 3 |
| 2.29 | 1 | 2 | 1 | 2 |
| 2.30 | 1 | 1 | 1 | 2 |
| 2.31 | 1 | 1 | 1 | 2 |
| 2.32 | 1 | 2 | 1 | 3 |
| 2.33 | 2 | 2 | 2 | 2 |
| 2.34 | 1 | 1 | 1 | 2 |
| 2.35 | 2 | 2 | 2 | 2 |
| 2.36 | 2 | 1 | 1 | 2 |
| 2.37 | 1 | 1 | 1 | 2 |
| 2.38 | 1 | 1 | 1 | 1 |
| 2.39 | 1 | 2 | 1 | 2 |
| 2.40 | 2 | 1 | 1 | 2 |
| 2.41 | 1 | 2 | 1 | 2 |
| 2.42 | 2 | 1 | 1 | 1 |
| 2.43 | 1 | 2 | 1 | 2 |
| 2.44 | 1 | 1 | 1 | 1 |
| 2.45 | 2 | 1 | 1 | 2 |
| 2.46 | 2 | 1 | 1 | 1 |
| 2.47 | 2 | 2 | 1 | 2 |
| 2.142 | 2 | 2 | 2 | 2 |
| 2.145 | 2 | 1 | 2 | 1 |
| 2.146 | 2 | 2 | 2 | 2 |
| 2.147 | 1 | 2 | 1 | 2 |
| 2.148 | 2 | 2 | 2 | 2 |
| 2.149 | 2 | 2 | 2 | 2 |

Example B2

Reduction in growth of tropical leguminous cover crops

The test plants (*Centrosema plumieri* and *Centrosema pubescens*) are cultivated to the fully grown stage, and then cut back to a height of 60 cm. After 7 days, the active ingredient is sprayed on in the form of an aqueous emulsion. The test plants are maintained at 70% relative humidity and with 6000 lux of artificial light, 14 hours per day, at temperatures of 27° C. by day and 21° C. by night. The test results are assessed 4 weeks after application of the emulsion. The new growth occurring compared with that on the control plants is estimated and weighed, and the phytotoxicity is evaluated. The plants treated with the active ingredients of the formula I show in this test a clear reduction in new growth (less than 20% of the new growth occurring on untreated control plants), without the test plants having suffered damage.

EXAMPLE B3

Regulation of growth of soya-bean plants

Soya-beans of the "Hark" variety are sown in plastic containers holding a soil/peat/sand mixture in the ratio of 6:3:1, and are placed into a climatic chamber. By optimum choice of temperature, illumination, fertiliser addition and watering, the plants develop over about 5 weeks into the 5-6 trifoliate stage. At this point, the plants are sprayed until thoroughly dripping wet with the aqueous liquor of an active ingredient of the formula I, the active-ingredient concentration being up to 100 g of active ingredient per hectare. An assessment of the results is made about 5 weeks after application of the active ingredient. The active ingredients of the formula I produce a marked increase in the number and in the weight of the pods on the leading shoots compared with the number and weight of pods on the untreated control plants.

EXAMPLE B4

Reduction in growth of cereals

The cereal varieties Hordeum vulgare (spring barley) and Secale (spring rye) are sown in plastics pots containing sterilised soil in a greenhouse, and watered as required. The young shoots are sprayed, about 21 days after sowing, with the aqueous spray liquor of an active ingredient of the formula I. The amount applied is up to 100 g of active ingredient per hectare, and 21 days after application, the growth of the cereals is assessed. The treated plants show a reduction in the extent of new growth compared with that on the untreated control plants (60-90% of the new growth on the control plants), and also in part an increase in the diameter of the stems of the plants. Example B5

Reduction of growth of grasses

The grasses *Lolium perenne, Poa pratensis, Festuca ovina, Dactylis glomerata* and *Cynodon dactylon* are sown, in a greenhouse, in plastics dishes containing a soil/peat/sand mixture (6:3:1), and watered as required. The emerged grasses are cut back weekly to a height of 4 cm, and are sprayed, about 50 days after sowing and one day after the final cutting, with the aqueous spray liquor of an active ingredient of the formula I. The amount of active ingredient corresponds, when converted, to up to 100 g per hectare. The growth of the grasses is assessed 21 days after application.

The compounds of the formula I effect a reduction of new growth of around 10-30%, compared with the new growth of the untreated control grasses.

What is claimed is:

1. An aminotriazine of the formula

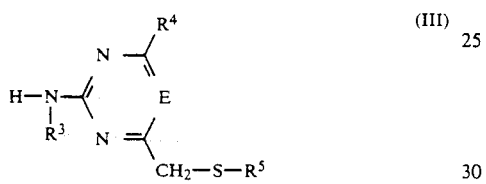

wherein

E is nitrogen,

Z is oxygen or sulfur, $R^3$ is hydrogen, $C_1$-$C_4$-alkyl, $C_3$-$C_4$-alkenyl or $C_1$-$C_4$-alkoxy, $R^4$ is hydrogen, halogen, $C_1$-$C_4$-alkyl, $C_1$-$C_4$haloalkyl, $C_1$-$C_4$-haloalkoxy, $C_1$-$C_4$-alkylthio, $C_2$-$C_4$alkoxyalkyl, $C_2$-$C_4$-alkoxyalkyl, cyclopropyl, $-NH_2$, $C_1$-$C_4$-alkylamino, di-$C_1$-$C_4$-alkylamino, or a saturated 5- to 7-membered nitrogen heterocycle bound by way of the nitrogen atom and selected from pyrrolidine, piperidine, morpholine, thiomorpholine, piperazine and hexamethyleneimine, $R^5$ is cyano, $-CZ-R^{13}$,

or an unsaturated heterocycle selected from imidazole, triazole, pyridine, pyrimidine, thiazole, oxazole, thiadiazole, oxadiazole, pyridiazine, thiophene or furan, as well as partially unsaturated derivatives thereof which are unsubstituted or substituted by a radical selected from the group consisting of halogen, $C_1$-$C_4$-alkyl, $C_1$-$C_4$-alkoxy and $C_1$-$C_4$-haloalkyl, $R^{13}$ is $C_1$-$C_4$-alkyl, $C_1$-$C_4$-alkoxy, $C_1$-$C_4$-alkylthio, phenyl, di-$C_1$-$C_4$-alkylamino, or a saturated 5- to 7-membered nitrogen heterocycle bound by way of the nitrogen atom and selected from pyrrolidine, piperidine, morpholine, thiomorpholine, piperazine and hexamethyleneimine and $R^{14}$ and $R^{15}$ independently of one another are $C_1$-$C_4$-alkyl, $C_1$-$C_4$-alkoxy, $C_3$-$C_4$-alkoxyalkoxy, $C_3$-$C_4$-alkenyloxy, $C_1$-$C_6$alkylamino or di-$C_1$-$C_4$alkylamino.

2. 2-Amino-4-methoxy-6-methoxythiocarbonylthiomethyl-1,3,5-triazine according to claim 1.

3. 2-Amino-4-methoxy-6-(N,N-dimethylthiocarbamoylthiomethyl)-1,3,5triazine according to claim 1.

* * * * *